(12) United States Patent
Buntz

(10) Patent No.: US 6,666,747 B1
(45) Date of Patent: Dec. 23, 2003

(54) METHOD FOR EMBELLISHING THE SHAPE OF A HUMAN BODY BY MEANS OF A COSMETIC PLASTER

(76) Inventor: Antonia Buntz, Siegfriedstrasse 20, D-80803 München (DE)

( * ) Notice: Subject to any disclaimer, the term of this patent is extended or adjusted under 35 U.S.C. 154(b) by 0 days.

(21) Appl. No.: 10/048,548

(22) PCT Filed: Aug. 2, 2000

(86) PCT No.: PCT/EP00/07491
§ 371 (c)(1), (2), (4) Date: May 31, 2002

(87) PCT Pub. No.: WO01/08515
PCT Pub. Date: Feb. 8, 2001

(30) Foreign Application Priority Data

Aug. 3, 1999 (DE) .......................... 199 36 395

(51) Int. Cl.[7] ................................. A41C 3/00
(52) U.S. Cl. ...................... 450/81; 450/1; 606/204.35; 424/400; 424/449
(58) Field of Search .............. 450/1, 39, 40, 450/57, 81; 128/890, 891, 892, 894; 602/41, 52, 54, 57, 58, 59, 903; 623/7; 606/204.35, 213–216; 424/400, 449

(56) References Cited

U.S. PATENT DOCUMENTS

| 1,783,512 A | | 12/1930 | Mather |
|---|---|---|---|
| 2,079,426 A | | 5/1937 | Schottenfels |
| 2,793,369 A | | 5/1957 | Panighini |
| 2,869,553 A | | 1/1959 | D'or |
| 3,276,449 A | | 10/1966 | Morgan |
| 4,343,313 A | | 8/1982 | Le Jeune |
| 4,432,347 A | * | 2/1984 | Clavin ............... 606/204.35 |
| 4,653,483 A | * | 3/1987 | Clavin ............... 606/204.35 |
| 4,982,450 A | | 1/1991 | D Huissier |
| 5,438,067 A | | 8/1995 | Jalonen et al. |
| 5,582,585 A | * | 12/1996 | Nash-Morgan ......... 602/41 |
| 5,961,986 A | | 10/1999 | Killen |
| 5,998,693 A | | 12/1999 | Zagame |
| 6,193,741 B1 | * | 2/2001 | Heavenridge et al. . 606/204.35 |

FOREIGN PATENT DOCUMENTS

| FR | 2388517 | 11/1978 |
|---|---|---|
| GB | 1435853 | 5/1976 |
| WO | 8000121 | 2/1980 |
| WO | 9709951 | 3/1997 |
| WO | 9834652 | 8/1998 |

* cited by examiner

Primary Examiner—Gloria Hale
(74) Attorney, Agent, or Firm—Stevens, Davis, Miller & Mosher, LLP

(57) ABSTRACT

A method for embellishing the shape of a human body utilizes a cosmetic plaster and suitable embodiments of cosmetic plasters. The cosmetic plaster is attached on the one hand, to skin over loose tissues (breast, abdomen, thighs, buttock) and on the other hand, to skin over firm tissues, preferably adjacent to human bone structure, so that the loose tissue parts are stretched towards the firm tissue parts. The plasters are used to lift the buttock, abdomen, breast and thighs in order to improve their aesthetics.

16 Claims, 5 Drawing Sheets

METHOD FOR EMBELLISHING THE SHAPE OF A HUMAN BODY BY MEANS OF A COSMETIC PLASTER

The invention relates to a method of beautifying the shape of the human body, as well as to tape as used for this purpose and to cosmetic tape suitably adapted for such use.

A wealth of cosmetic procedures and products are available for beautifying the human body. "Cosmetic" in this sense is understood to be the art of retaining, enhancing and reinstating the beauty of the human body (as defined in the 18th Edition of the German encyclopaedia "Große Brockhaus", 1979). In its most extended sense this is understood to also include, for example, items of underwear to the extent that these are intended to model certain parts of the body into a more appealing shape, such as for instance push-up bras. In a more constricted sense, cosmetics relates to skin beautification.

Known from German utility model DE 88 11 658 U1, for example, is a skin dress made of a self-adhesive material externally adapted to the skin and with which wrinkles, scars or blemishes in the skin can be concealed.

Known furthermore from German patent DE 43 30 506 A1 is a tape for combating premature wrinkling and dry skin by active constituents being dispensed from the tape or from a vehicle attached thereto of flexible plastics to the skin. For this purpose, the skin site to be treated is spread by two fingers and the tape applied so that the active constituents can gain access to the site to be smoothed and dilated.

The cited aspects merely serve, however, to beautifying the skin of the human body, they failing to achieve a more attractive bodily shape. It is only in a long-term consideration that such aspects permit beautifying the shape of the body. Beautifying the shape of more particularly sagging large surface area sites such as on the breast, tummy, buttocks, thighs, etc as the typical problem areas is not attainable therewith at short notice.

The objective of the present invention is to beautify the shape of particular sites of the human body, a further objective being the cosmetic beautification of the skin itself.

This objective is achieved in accordance with the invention by the features of the parallel method, product and use claims. Advantageous further embodiments of the invention read from the corresponding sub-claims.

The invention is based on the basic principle of tape-lifting sagging tissue sites to taut or firm tissue sites, it being due to the change in the outer shape of the sagging tissue sites that the sagging tissue is visually tautened. The visual effect of this is most intensive when tautening is opposite the force of gravity, i.e. when the sagging tissue is lifted in an upright bodily posture. For this purpose a cosmetic tape is adhered to a skin site covering the sagging tissue, at one end, and to a skin site covering the firm tissue, at the other end, so that it is tensile stressed, the first attachment location covering the sagging tissue site being arranged above the second attachment location covering the firm tissue site. Preferably the second attachment location is in the immediate vicinity of a bone or cartilage site of the human body.

It is in this way that breast, tummy, buttocks, thigh tissue sites can be lifted into a more attractive, tautened shape. Bras and panties incorporated lifting devices can now be eliminated and simply replaced as described taped, this applying more particularly to nipple enhancement by lifting. Chafing due to bras and panties incorporated lifting devices no longer occurs in thus adding to the visual appeal. However, it is just as possible to make use of the cosmetic tape in addition to bras and panties for extra support, for example, in sports or similar activities.

The cosmetic tape is suitably for both short-term and long-term use and is worn preferably between a few hours and 3 days.

Preferred properties of the cosmetic tape are resistance to water, permeable to air and moisture, extremely thin, transparent or at least tissue-coloured, elastic, adhesive substantially over the full surface of the tape (preferably at least between the attachment locations), and scented.

The resistance to water enables the wearer to shower and bathe without needing to change the cosmetic tape for a number of days.

The permeability to air and moisture is of advantage in retaining the respiration function of the tissue. For this purpose the backing of the tape is fine pored, and the adhesive surface area is also configured discontinuous, for example in a netted configuration or pored.

Configuring the cosmetic tape thin is of advantage for the visual impression, i. e. it needing to be as thin as possible so that its outline is not discernible through close-fitting garments, for example T shirts, bodies, etc.

It is of advantage when the cosmetic tape is transparent so that it is not discernible under see-through garments and is not immediately apparent when exposed to view by a garment slipping out of place. Skin-coloured cosmetic tape is suitably although not as suitably as transparent material due to the colour nuances of the skin.

The elasticity of the cosmetic tape is likewise of great advantage in preventing the tissue site under the cosmetic tape from being absolutely affixed as regards neighbouring tissue areas. Such an absolutely affixed location could become evident on hasty body movements by the the neighbouring tissue areas being displaced relative to the affixed tissue site. The elasticity of the cosmetic tape material enables the cosmetic tape to act as an expander between the two attachment locations, the function of the cosmetic tape, namely to lift sagging tissue sites, being assured at all times. Apart from this, a non-elastic cosmetic tape would result in a creasing nuisance, depending on the body posture.

Configuring the cosmetic tape adhesive substantially over the full surface of the tape is particular of advantage in such applications involving a concave curvature of the body surface between the two attachment locations. In such cases the cosmetic tape would otherwise lift off from the skin surface between the attachment locations. Providing the tape adhesive throughout is thus particular of advantage when the cosmetic tape is used as a breast push-up, but just as feasible for other applications.

Tegaderm™ made by the 3m Company is a material suitable for the cosmetic tape, for example.

Scenting the cosmetic tape enables it to satisfy additional functions, for example, as a deodorant.

It is furthermore of advantage when active constituents are added to the cosmetic tape for gradual dispensing to the tissue. These active constituents could be defined, for example, to assist the function of the tissue in combating cellulitis or for other purposes. For combating cellulitis camphor or eucalyptus preparations may be admixed in the cosmetic tape. Other active constituents coming into consideration are, for example, vitamins, minerals, herbal essences, etc.

A few advantageous aspects of the cosmetic tape in accordance with the invention will now be described by way of example with reference to the drawings in which.

Figure 1:
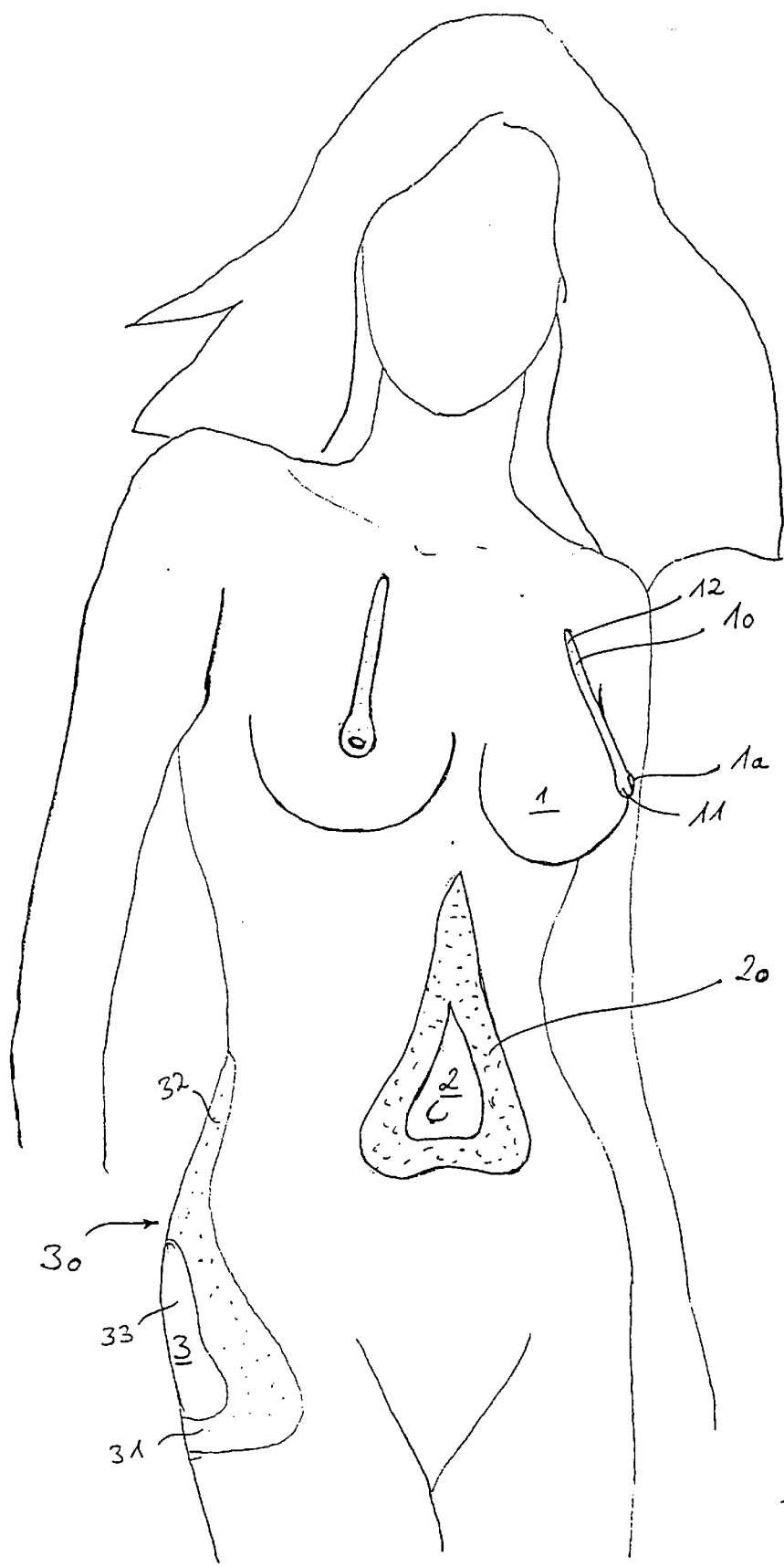
FIG. 1 is an illustration of a human body including cosmetic tapes in accordance with the invention at various sites on the body.

Referring now to FIG. 1 there is illustrated the body of a woman taped with three different embodiments of the cosmetic tape in accordance with the invention. One cosmetic tape 10 is secured to each breast 1 of the human body. In this arrangement, a first attachment location 11 of the cosmetic tape 10 surrounds the nipple 1a. The second attachment location 12 of the cosmetic tape 10 is affixed in the vicinity of the collar bone, since this skin site is subjected to comparatively little movement relative to the underlying bone structure of the human body. To prevent the cosmetic tape 10 from detaching from the surface of the body between the first and second attachment locations 11, 12 the cosmetic tape 10 is in adhesive contact with the skin throughout.

Figures 2A, 2B:
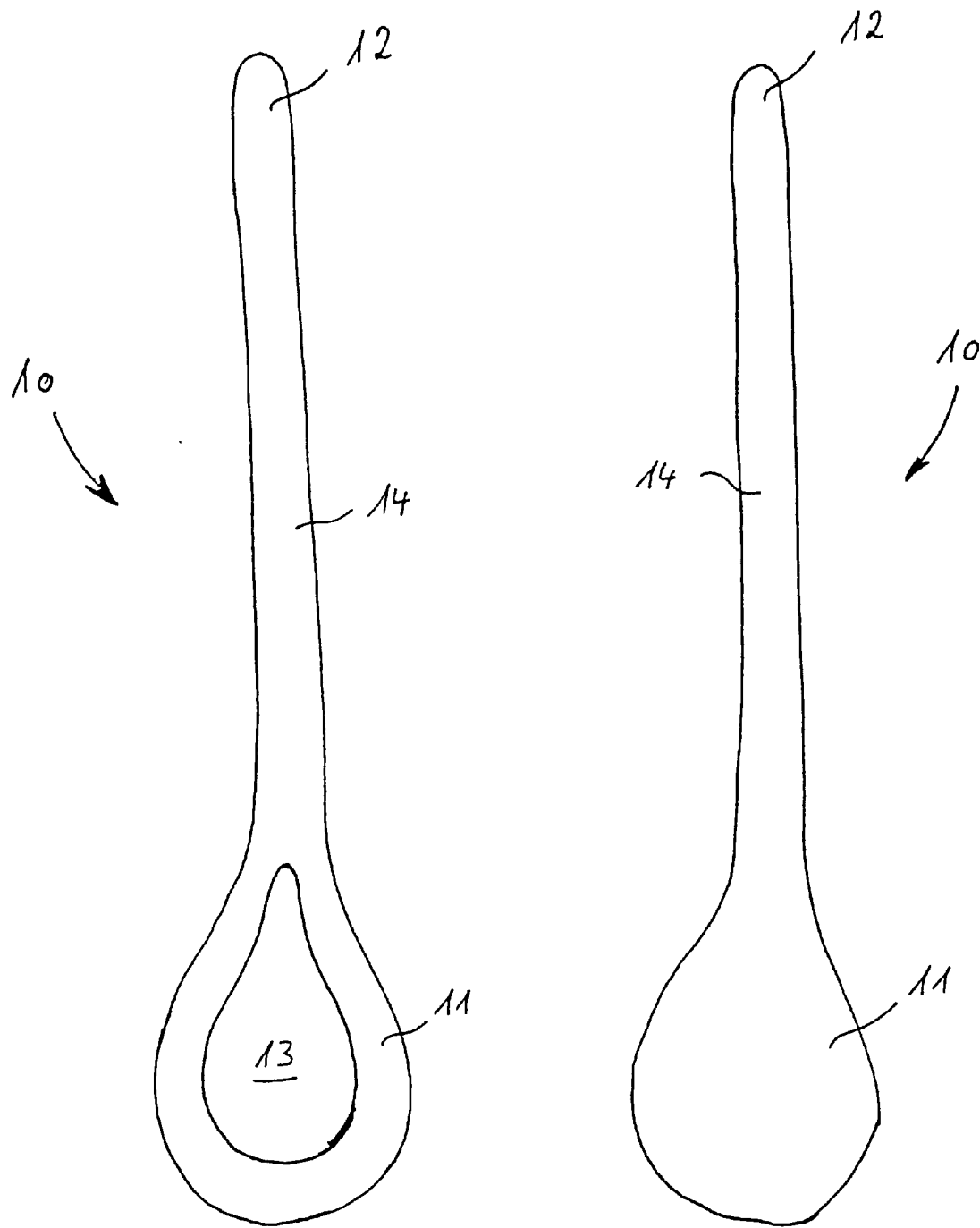
FIGS. 2a and 2b are illustrations of cosmetic tapes in accordance with the invention for breast lifting.

Referring now to FIGS. 2a and 2b there are illustrated two cosmetic tapes 10, one for lifting the breast and the other for enhancing prominence of the nipple. Unlike normal plaster tape it is of advantage when the first attachment location 11 to be affixed to the sagging tissue is configured comparatively wide, the tape then being tapered to the second attachment location 12. Put very simply, one could term this a triangular shape. However, the second attachment location must not necessarily form the narrowest part of the tape, although as a rule it is narrower than the first attachment location.

This basic structure also applies to the other cosmetic tapes in accordance with the invention. This structure is, however, not mandatory for implementing the method in accordance with the invention. Instead, conventional shapes of plaster tape may also be employed.

The cosmetic tape 10 as shown in FIG. 2a comprises an opening 13 having a width of approx. 25 mm, through which the nipple 1a (FIG. 1) protrudes. This substantially enhances the prominence of the nipple 1a in more particularly adding to the erotic appeal thereof. In this case the cosmetic tape 10 has the shape of a bottle opener. The width of the loop formed by the opening 13 is approx. 7 mm whilst the web 14 leading to the second attachment location 12 is approx. 10 mm wide. The overall length of the cosmetic tape 10 is approx. 160 mm.

Referring now to FIG. 2b there is illustrated how the opening 13 may also be eliminated, however, so that the cosmetic tape 10 for breast lifting has more the shape of a spoon. This embodiment is devised for women not wishing to enhance the prominence of the nipple.

Figure 3:
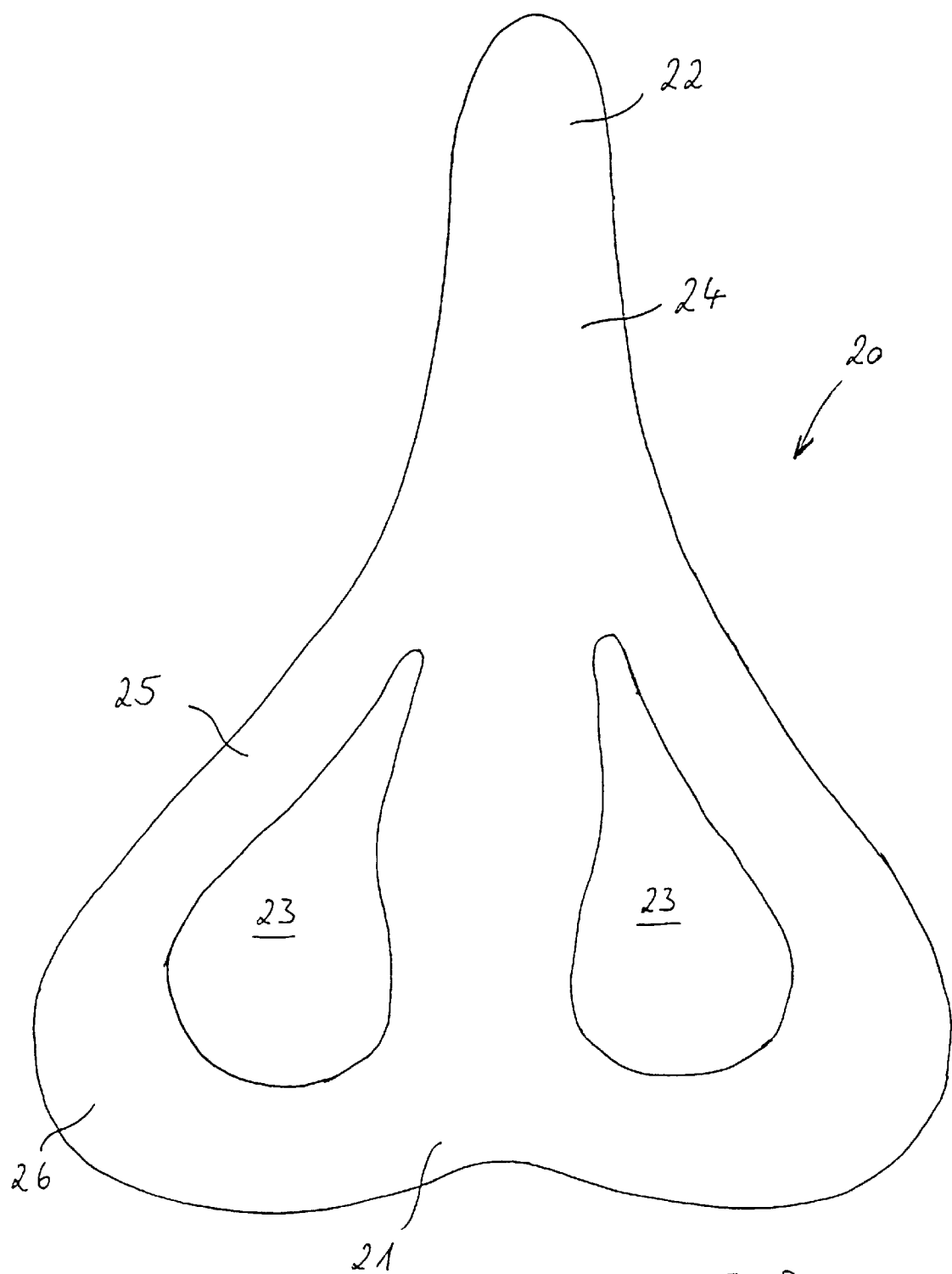
FIG. 3 is an illustration of a cosmetic tape in accordance with the invention for visually tautening a tummy site of the human body.

Referring now to FIG. 3 there is illustrated a cosmetic tape 20 for lifting a tummy site 2 which is just as suitable, however, also for lifting the thigh 3 and even for the buttocks to a certain extent. Here too, the first attachment location 21 of the cosmetic tape 20 is configured wide to cover the lower tummy site, before then running upwards narrow to end in the second attachment location 22. Likewise provided is an opening 23. The opening has more particularly the purpose of adding to the comfort of wearing the cosmetic tape, since the less tape in contact with the skin the better. Whilst the first attachment location 21 of the cosmetic tape 20 is secured below the navel of the person wearing it, the second attachment location 22 is secured in the vicinity of the solar plexus. The preferred embodiment of the cosmetic tape 20 for lifting the tummy is approximately pear-shaped, where necessary cusped in the lower first attachment location 21, as shown in FIG. 3.

The cosmetic tape 20 is approx. 125 mm long. The web 24 is approx. 30 mm wide and the loops formed by the opening 23 have a width of approx. 20 mm in the upper region of the loop 25 and a width of approx. 25 mm in the lower region of the loop 26.

The cosmetic tape 30 for tautening the exterior of the thigh 3 has basically the same configuration as the cosmetic tape 20 for lifting the tummy, and is thus not illustrated separately. As evident from FIG. 1 the second attachment location 32 is affixed in the vicinity of the hip bone at the waist roughly level with the navel.

Figure 4A:
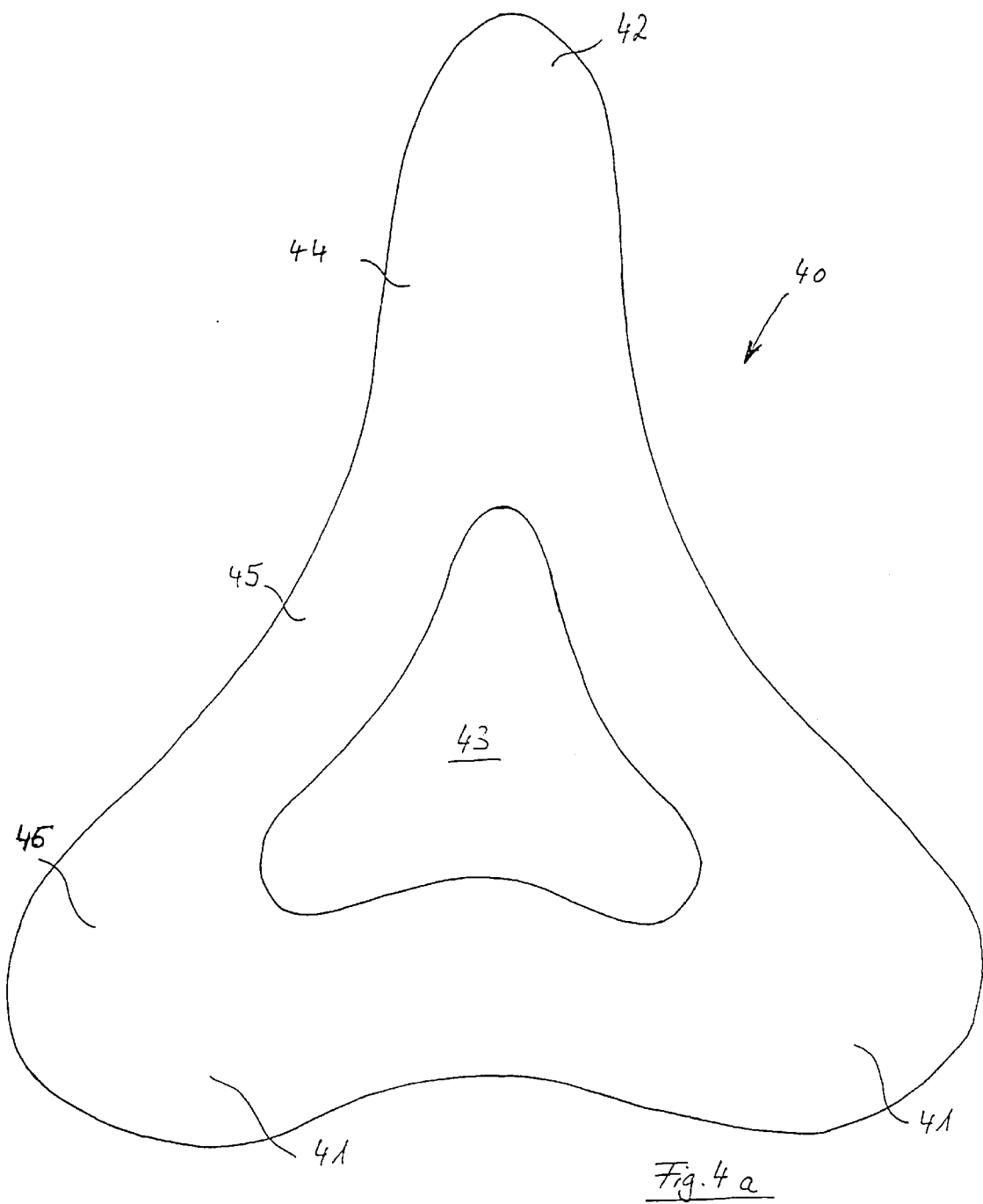
FIGS. 4a and 4b are illustrations of cosmetic tapes in accordance with the invention for lifting the buttocks of the human body.
Figure 4B:
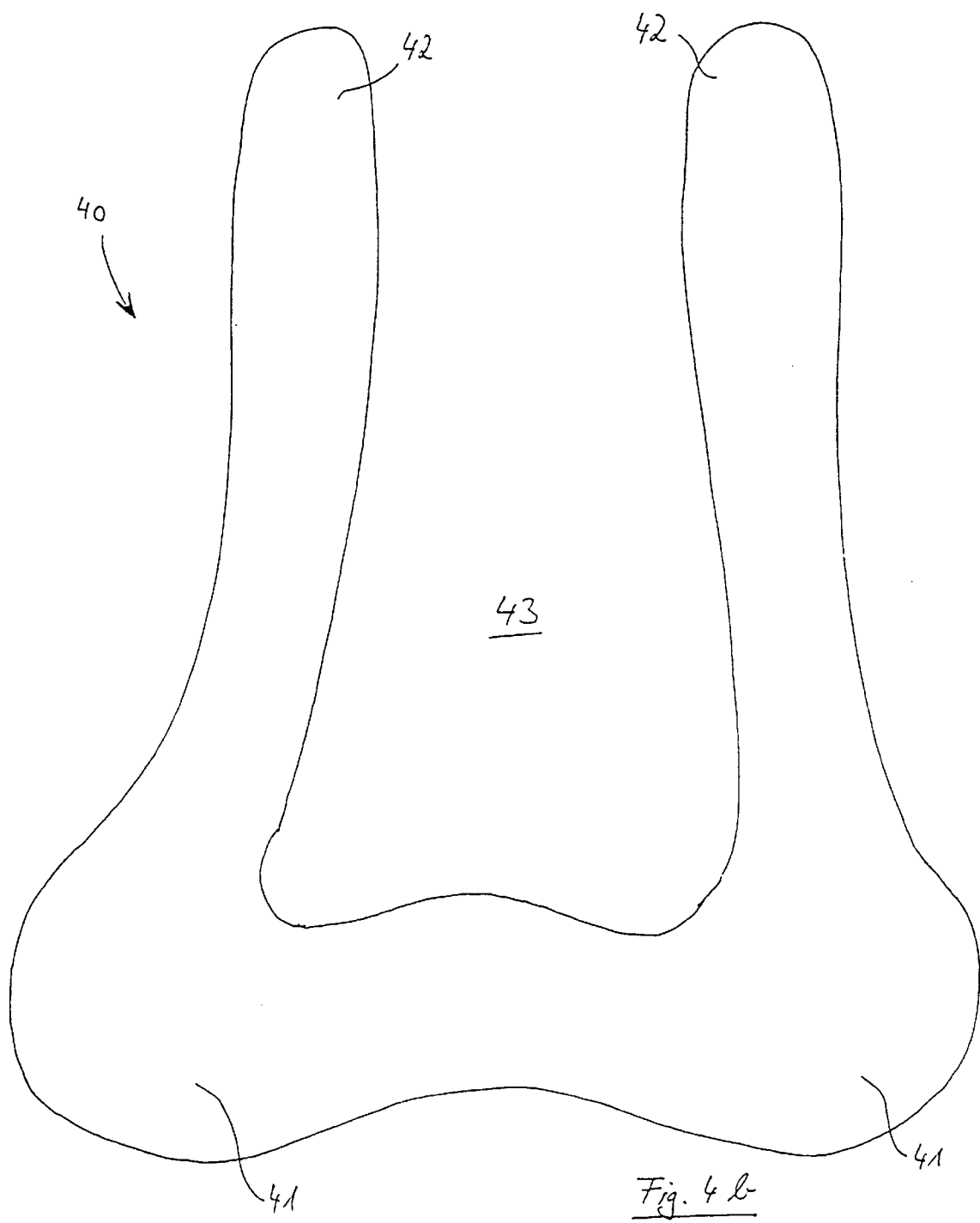

Referring now to FIGS. 4a and 4b there are illustrated two embodiments of cosmetic tape for lifting more particularly the buttocks, although they are just as suitable for tummy and thigh use. The first attachment location 41 is affixed to the buttock sites whilst the second attachment location 42, depending on the embodiment, is secured either to the spine roughly level with the coccyx (FIG. 4a) or to the left and right of the spine at the groin locations (FIG. 4b). These embodiments can thus be termed heart-shaped or W-shaped. The heart-shaped embodiment as shown in FIG. 4a is approx. 200 mm long as measured on the longitudinal centerline and approx. 180 mm wide at the broadest location. The width of the web 44 is 45 mm, whilst the width of the loop formed by the opening 43 in the upper portion of the loop 45 is approx. 30 mm and in the lower portion of the loop 46 it is approx. 55 mm.

What is claimed is:

1. A method of lifting a female breast having a nipple by means of a tape, said tape having a first end defining a lower attachment location for adhesively attaching to at least one first skin location on a human body over sagging tissue of said female breast and a second end defining an upper attachment location for adhesively attaching to at least one second skin location on said human body over firm tissue;

said lower attachment location being wider than said upper attachment location and comprising an opening which gives said lower attachment location the shape of a loop;

said tape being attached to said human body such that said upper attachment location is affixed to said second skin location over firm tissue and said lower attachment location surrounds said nipple protruding through said opening, thereby drawing said sagging tissue of said female breast against the force of gravity in an upright body posture in the direction of said firm tissue.

2. The method as set forth in claim 1, wherein said upper attachment location is located in the immediate vicinity of a bone or cartilage site of said human body.

3. The method as set forth in claim 1, wherein said upper attachment location is located in the vicinity of the collar bone of said human body.

4. The method as set forth in claim 1, wherein said tape is adhesively attached full-length between said lower attachment location and said upper attachment location.

5. The method as set forth in claim 1, wherein said tape is so thin that it is non-discernible under close-fitting garments.

6. A cosmetic tape for lifting a female breast having a nipple, comprising:

a first end defining a lower attachment location for adhesively attaching to at least one first skin location on a human body over sagging tissue of said female breast;

a second end defining an upper attachment location for adhesively attaching to at least one second skin location on said human body over firm tissue;

said lower attachment location being wider than said upper attachment location and comprising an opening which gives said lower attachment location the shape of a loop.

7. The cosmetic tape as set forth in claim 6 which is made of an elastic material allowing said cosmetic tape to act as an expander between said lower attachment location and said upper attachment location.

8. The cosmetic tape as set forth in claim 1 which is adhesively attached full-length between said lower attachment location and said upper attachment location.

9. The cosmetic tape as set forth in claim 6 which is transparent.

10. The cosmetic tape as set forth in claim 6 which is so thin that it is non-discernible under close-fitting garments.

11. The cosmetic tape as set forth in claim 6 which is water-resistant.

12. The cosmetic tape as set forth in claim 6 which is air-permeable.

13. The cosmetic tape as set forth in claim 6 which is moisture-permeable.

14. The cosmetic tape as set forth in claim 6 which contains active constituents.

15. The cosmetic tape as set forth in claim 6 which is scented.

16. Use of the cosmetic tape as set forth in claim 6 for lifting a female breast having a nipple, wherein said cosmetic tape is attached to said human body such that said upper attachment location is affixed to said second skin location over firm tissue and said lower attachment location surrounds said nipple protruding through said opening, thereby drawing said sagging tissue of said female breast against the force of gravity in an upright body posture in the direction of said firm tissue.

* * * * *